(12) United States Patent
Moshier et al.

(10) Patent No.: US 10,474,791 B2
(45) Date of Patent: Nov. 12, 2019

(54) METHODS AND SYSTEMS FOR BIOMETRIC IDENTIFICATION OF DAIRY ANIMALS USING VEIN PATTERN RECOGNITION

(71) Applicant: SRC, Inc., North Syracuse, NY (US)

(72) Inventors: Timothy Francis Moshier, Fulton, NY (US); Kenton Arthur Doctor, East Syracuse, NY (US); Stephanie A. C. Schuckers, Canton, NY (US); Sean K. Banerjee, Hannawa Falls, NY (US); Boyang Li, Potsdam, NY (US)

(73) Assignee: ACUMEN DETECTION, INC., Cazenovia, NY (US)

( * ) Notice: Subject to any disclaimer, the term of this patent is extended or adjusted under 35 U.S.C. 154(b) by 0 days.

(21) Appl. No.: 15/712,370

(22) Filed: Sep. 22, 2017

(65) Prior Publication Data

US 2018/0082016 A1    Mar. 22, 2018

Related U.S. Application Data

(60) Provisional application No. 62/398,138, filed on Sep. 22, 2016.

(51) Int. Cl.
*A61B 5/0205* (2006.01)
*G06F 16/583* (2019.01)
(Continued)

(52) U.S. Cl.
CPC ............ *G06F 19/30* (2013.01); *A01K 11/006* (2013.01); *A61B 5/02055* (2013.01); *A61B 5/04* (2013.01);
(Continued)

(58) Field of Classification Search
None
See application file for complete search history.

(56) References Cited

U.S. PATENT DOCUMENTS

| 5,787,185 A | 7/1998 | Clayden |
| 6,320,973 B2 | 11/2001 | Suzaki et al. |
| (Continued) | | |

FOREIGN PATENT DOCUMENTS

| WO | 03055297 | 7/2003 |
| WO | 2006067226 | 6/2006 |
| (Continued) | | |

OTHER PUBLICATIONS

International Search Report Form PCT/ISA/220, International Application No. PCT/US2017/052874, pp. 1-12, dated Nov. 30, 2017.
(Continued)

*Primary Examiner* — Idowu O Osifade
(74) *Attorney, Agent, or Firm* — Bond Schoeneck & King, PLLC; George McGuire

(57) ABSTRACT

A method for identifying a dairy animal, the method comprising the steps of: providing an identification system comprising an imaging device and a database of stored vein patterns; obtaining at least one image of at least a portion of an udder of the dairy animal; extracting a vein pattern from the at least one image; comparing the extracted vein pattern to the database of stored vein patterns; and identifying, based on said comparison, the dairy animal in the database of stored vein patterns.

20 Claims, 4 Drawing Sheets

(51) Int. Cl.
　　*G06F 19/00*　　(2018.01)
　　*A61B 5/04*　　(2006.01)
　　*A01K 11/00*　　(2006.01)
(52) U.S. Cl.
　　CPC ...... *G06F 16/583* (2019.01); *A01K 2227/101* (2013.01); *A61B 2503/40* (2013.01)

(56) References Cited

U.S. PATENT DOCUMENTS

| | | | |
|---|---|---|---|
| 6,532,892 | B1 | 3/2003 | Nilsson |
| 8,185,747 | B2 | 5/2012 | Wood et al. |
| 8,794,182 | B2 | 8/2014 | Eineren |
| 9,084,411 | B1 | 7/2015 | McGlone et al. |
| 2007/0237365 | A1 | 10/2007 | Monro |
| 2010/0143265 | A1* | 6/2010 | Hewes .................. A01N 25/16 424/43 |
| 2010/0317094 | A1* | 12/2010 | Ricco .................. G01N 33/04 435/287.2 |
| 2015/0302241 | A1 | 10/2015 | Eineren et al. |

FOREIGN PATENT DOCUMENTS

| | | |
|---|---|---|
| WO | 034377 | 3/2015 |
| WO | 140780 | 9/2015 |

OTHER PUBLICATIONS

Harrell, Ryan J., et al., "Identification of Swine by Auricular Vein Patterns", Jul. 18, 2008, 15 pages.

Tharwat, Alaa, et al., "Cattle Identification using Muzzle Print Images based on Texture Features Approach", (2014) Proceedings of the Fifth International Conference on Innovations in Bio-Inspired Computing and Applications IBICA 2014. Advances in Intelligent Systems and Computing, vol. 303. Springer, Cham; 11 pages.

* cited by examiner

200

```
┌─────────────────────────────────────────────────────┐
│   Provide a device comprising an imaging component  │
│                        210                          │
└─────────────────────────────────────────────────────┘
                          ⇓
┌─────────────────────────────────────────────────────┐
│ Capture an image of at least a portion of an udder of a dairy animal │
│                        220                          │
└─────────────────────────────────────────────────────┘
                          ⇓
┌─────────────────────────────────────────────────────┐
│     Extract a vein pattern from the one or more images     │
│                        230                          │
└─────────────────────────────────────────────────────┘
                          ⇓
┌─────────────────────────────────────────────────────┐
│  Compare the extracted vein pattern to a database of vein patterns  │
│                        240                          │
└─────────────────────────────────────────────────────┘
                          ⇓
┌─────────────────────────────────────────────────────┐
│     Identify, based on the comparison, the imaged animal     │
│                        250                          │
└─────────────────────────────────────────────────────┘
                          ⇓
        ┌─────────────────────────────────────┐
        │ Associate data/information with the identified animal │
        │                 260                 │
        └─────────────────────────────────────┘
                          ⇓
   ┌─────────────────────────────────────┐
   │    Collect a milk sample from the animal    │
   │                 270                 │
   └─────────────────────────────────────┘
                          ⇓
        ┌─────────────────────────────────────┐
        │   Make a management decision about the animal   │
        │                 280                 │
        └─────────────────────────────────────┘
```

FIG. 2

METHODS AND SYSTEMS FOR BIOMETRIC IDENTIFICATION OF DAIRY ANIMALS USING VEIN PATTERN RECOGNITION

CROSS-REFERENCE TO RELATED APPLICATION

This application claims priority to U.S. Patent Application Ser. No. 62/398,138, filed on Sep. 22, 2016, and entitled "Methods and Systems for Biometric Identification of Dairy Animals Using Vein Pattern Recognition," the entire disclosure of which is incorporated herein by reference.

FIELD OF THE INVENTION

The present disclosure is directed generally to a method for characterizing, identifying, and tracking a dairy animal using vein pattern imaging and recognition.

BACKGROUND

As farming operations grow, particularly dairy operations, there is an accompanying requirement for accurate data critical to precision management. Efficient animal tracking and maintenance, for example, is essential for a dairy farm of any size.

Among many other conditions and situations that require efficient animal tracking and maintenance, on-farm pathogen identification systems ensure accurate identification of infected and treated animals. Providing readily-available and actionable information to operation managers enables on-the-spot treatment, disposition, and/or other remediation decisions. For example, the identification and tracking of mastitis is an important component of animal tracking. Mastitis is the name given to inflammation of udder tissue due to infection, which can be caused by a number of different pathogens including *Staphylococcus aureus, S. epidermidis*, and others. Accurately associating an animal's identification with results of her mastitis test enables targeted antibiotic treatment and overall reduced use of antibiotics in farm animals, rapid culling of animals with contagious forms of mastitis, and ultimately reduced revenue losses to the farmer. Of vital importance is accurate identification and tracking of the animal from the moment she is identified as mastitic through the period she is treated (and/or isolated), to the point where her milk is suitable for sale. Too frequently cows are misidentified/tracked, and either their mastitic milk enters the bulk tank (degrading the overall quality and price of that batch of milk), or worse, an antibiotic-treated animal's milk is added to the bulk tank, resulting in the rejection of the entire load of milk by the processing plant, or conveyance of that antibiotic to the general population.

Dairy animal identification and tracking, however, can be difficult. In traditional farming operations, during milking time the dairy animal enters the milking parlor and backs into or walks into a milking stanchion. Typically, the milker/herdsman will see only a limited portion of the animal when the animal is in the milking station; i.e., the rear of the animal from her feet to near the top of her udder. Often, the animal's unique identification is her ear-tag, which is located seven to eight feet from the milker, and blocked from view. Even farms that utilize RFID ear tags and RFID readers in their milking parlors are plagued with misidentifications, as the cows' head movements cause erroneous RFID reads by adjacent milking stations. The milker may then visually inspect the udder to see if it is inflamed and/or express a small amount of milk to see if it shows signs of mastitis disease, such as watery or clotted milk. If it looks like the animal has mastitis, the animal will be identified and/or tagged. For example, among many other options, a leg band may be wrapped around the animal's leg and her milk will be separated from the rest of the collected milk. That cow will then go back to the herd, field, or barn, and it may be challenging to find which animal out of a herd of hundreds or more has the tag or leg band. Unfortunately, leg bands are susceptible to being torn off either by the cow's own movement, or by being stepped on by one of her herd mates. Without the leg band, the milker will not know if the cow needs to be treated, and her milk separated.

It would be advantageous to have methods and systems in place to quickly identify and then track an animal that may have symptoms of mastitis or other tracked conditions. This could then be utilized to notify milkers when the animal is entering a stanchion or parlor, enabling isolation of the collected milk.

Accordingly, there is a continued need in the art for methods and systems for improved characterization, identification, and tracking of dairy animals using a biometric unique to the individual animal, is stable over time, is easily accessible to the milking technician or herdsman, and rapidly identifies the animal before milking begins.

SUMMARY OF THE INVENTION

The present disclosure is directed to an inventive method for udder vein pattern imaging and animal identification. Various embodiments and implementations herein are directed to a method for obtaining an image of a dairy animal's udder, extracting a vein pattern, and identifying the animal using the extracted pattern by comparing the pattern to a database of vein patterns. The system and method may then be used to associate information, such as a medical condition or other information, to the identified animal.

Generally, in one aspect, a method for identifying a dairy animal using a computing device comprising an imager is provided. The method includes the steps of: (i) obtaining, via the imager of the computing device, at least one image of at least a portion of an udder of the dairy animal; (ii) extracting a vein pattern from the at least one image; (iii) comparing the extracted vein pattern to a database of stored extracted vein patterns, wherein each extracted vein pattern in the database is associated with an animal in a herd of dairy animals; and (iv) identifying, based on the comparison, the dairy animal in the database of stored extracted vein patterns.

According to an embodiment, the method further includes the step of communicating the obtained at least one image to a central herd management computing device for the extracting, comparing, and/or identifying step(s).

According to an embodiment, the computing device is a handheld computing device. According to an embodiment, the computing device is a tablet or smartphone.

According to an embodiment, the method further includes the step of prompting a herd manager, if the extracted vein pattern does not match any of the stored extracted vein patterns, for information about the imaged dairy animal.

According to an embodiment, the imager is a camera, a near-infrared spectroscope, or a thermal imager.

According to an embodiment, the method further includes the step of selecting, based at least in part on the identification of the dairy animal, a management decision about the identified dairy animal.

According to an embodiment, the method further includes the step of associating, based at least in part on the identification of the dairy animal, additional information about the identified animal in the database of stored extracted vein patterns.

In another aspect, a system for identifying a dairy animal is provided. The system includes: a database of stored extracted vein patterns, wherein each stored extracted vein pattern is associated with a specific dairy animal; a computing device comprising an imager configured to obtain at least one image of at least a portion of an udder of the dairy animal; and a controller configured to: (i) extract a vein pattern from the at least one obtained image; (ii) compare the extracted vein pattern to one or more extracted vein patterns in the database of stored extracted vein patterns; and (iii) identify, based on said comparison, the dairy animal in the database of stored extracted vein patterns.

According to an embodiment, the system further includes a communications module configured to communicate the obtained at least one image.

According to an embodiment, the system is a herd management system, and wherein said computing device comprises a handheld computing device. According to an embodiment, the computing device is a tablet or smartphone.

According to an embodiment, the controller is further configured to prompt a user, if the extracted vein pattern does not match any of the stored extracted vein patterns, for information about the imaged dairy animal.

According to an embodiment, the imager is a camera, a near-infrared spectroscope, or a thermal imager.

According to an embodiment, the controller is further configured to receive a selection from a user comprising a management decision about the identified dairy animal, wherein said management decision is based at least in part on the identification of the dairy animal.

According to an embodiment, the controller is further configured to associate, based at least in part on the identification of the dairy animal, additional information about the identified animal in the database of stored extracted vein patterns.

In another aspect, a herd management computing device is provided. The device includes: an imager configured to obtain at least one image of at least a portion of an udder of the dairy animal; and a controller configured to: (i) extract a vein pattern from the at least one obtained image; (ii) compare the extracted vein pattern to one or more extracted vein patterns in a database of stored extracted vein patterns, wherein each stored extracted vein pattern is associated with a specific dairy animal; and (iii) identify, based on said comparison, the dairy animal in the database of stored extracted vein patterns.

According to an embodiment, the herd management computing device is a tablet or smartphone.

According to an embodiment, the controller is further configured to receive a selection from a user comprising a management decision about the identified dairy animal, wherein said management decision is based at least in part on the identification of the dairy animal.

According to an embodiment, the controller is further configured to associate, based at least in part on the identification of the dairy animal, additional information about the identified animal in the database of stored extracted vein patterns.

These and other aspects of the invention will be apparent from the embodiments described herein.

BRIEF DESCRIPTION OF THE DRAWINGS

The present invention will be more fully understood and appreciated by reading the following Detailed Description in conjunction with the accompanying drawings, in which:

FIG. 2 is a flowchart of a dairy animal identification and tracking method, in accordance with an embodiment.

DETAILED DESCRIPTION

The present disclosure describes various embodiments of a system and method for udder vein pattern imaging and animal identification. Various embodiments and implementations herein are directed to a method for obtaining an image of a dairy animal's udder, extracting a vein pattern, and identifying the animal using the extracted pattern by comparing the pattern to a database of vein patterns. The system and method enable repeatable precise and rapid animal identification so information, such as a medical condition or other information, can be accurately associated with the identified animal.

Figure 1:
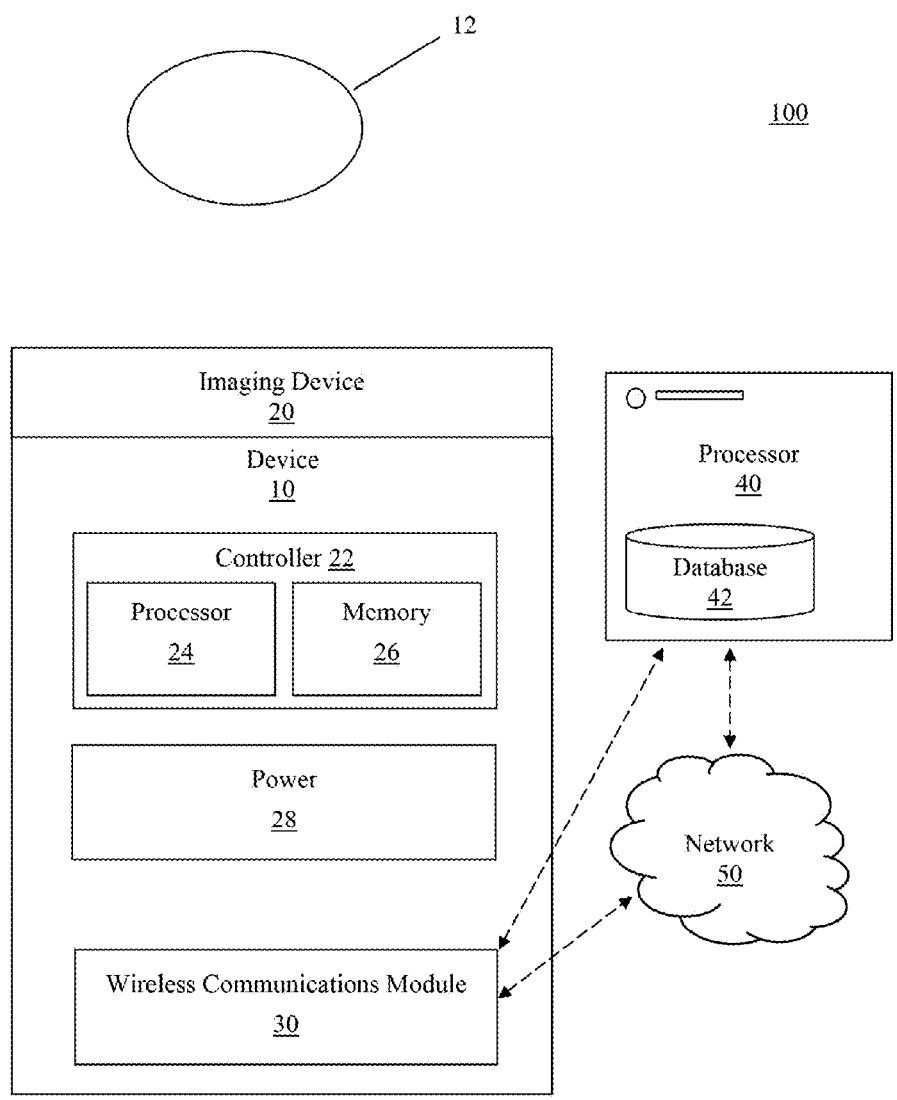
FIG. 1 is a schematic representation of a system for dairy animal identification and tracking, in accordance with an embodiment.

Referring to FIG. 1 is a schematic representation of a system 100 for dairy animal identification and tracking, in accordance with an embodiment. According to an embodiment, system 100 is configured to obtain an image of at least a portion of an udder 12 of a dairy animal, where the dairy animal is any animal that provides milk used by humans, including but not limited to cow, buffalo, goat, sheep, camel, donkey, horse, reindeer, and yak.

According to an embodiment, system 100 includes a mounted, portable, or handheld computing device 10 that is utilized to obtain an image of at least a portion of an udder 12 of a dairy animal. For example, device 10 may be a laptop, desktop computer, tablet, smartphone, wearable, smart camera, or other computing device. According to an embodiment, device 10 is a herd management computing device, and/or networked to or otherwise in communication with a herd management computing system, where the herd management device or system is configured to facilitate Device 10 includes an imager or component 20 which is configured to capture one or more images of at least a portion of an udder 12 of a dairy animal. According to an embodiment, the imager 20 is a camera, a near-infrared spectroscope, a thermal imager, and/or any other type of camera or imager sufficient to capture information about a vein pattern of the udder 12. The imager may be connected to a controller 22, and transmits the captured image information to the controller and/or via a wireless communications module 30. The wireless communications module 30 can be, for example, Wi-Fi, Bluetooth, IR, radio, or near field communication that is positioned in communication with controller 22 or, alternatively, controller 22 can be integrated with the wireless communications module.

Controller 22 can be configured or programmed to capture images of an udder 12 using imager 20. Controller 22 can be or have, for example, a processor 24 programmed using software to perform various functions discussed herein, and can be utilized in combination with a memory 26. Memory 26 can store data, including one or more captured images or software programs for execution by processor 24, as well as various types of data including but not limited to information about specific animals. For example, the memory 26 may be a non-transitory computer readable storage medium that includes a set of instructions that are executable by processor 24, and which cause the system to execute one or more of the steps of the methods described herein.

Device 10 also includes a source of power 28, most typically DC power, although other power sources are possible including AC power sources, solar-based power sources, or mechanical-based power sources, among others. The power source may be in operable communication with a power source converter that converts power received from an external power source to a form that is usable by the lighting unit. In order to provide power to the various components of device 10, it can also include an AC/DC converter (e.g., rectifying circuit) that receives AC power from an external AC power source 28 and converts it into direct current for purposes of powering the light unit's components. Additionally, device 10 can include an energy storage device, such as a rechargeable battery or capacitor, that is recharged via a connection to the AC/DC converter and can provide power to controller 22 and imager 20 when the circuit to AC power source 28 is opened.

According to an embodiment, system 100 also comprises a central processor 40 with a database 42. The central processor 40 may be a parlor-level and/or farm-level, and/or enterprise-level central processor, which will collect information from a parlor, an entire farm, or an entire enterprise. The central processor 40 may be programmed or configured to execute some or all functionality of the method described herein. According to an embodiment, central processor 40 may communicate with device 10 directly via a wired and/or wireless communications link, and/or via a wireless network 50.

For example, according to an embodiment, central processor 40 is a component of a central herd management system, server, or computer. The central herd management system may comprise a system configured to facilitate one or more functions of herd management, including but not limited to animal tracking and/or animal identification. Accordingly, the central herd management system may comprise a centralized or primary computing center, server, or computer, and one or more remote or secondary computing devices which are in communication with the primary computing center but enable remote functionality such as image capture, animal, tracking, and/or animal identification. For example, the herd management system may comprise a backroom computer or server, or a remotely located computer or server in the case of a SAAS solution, and can comprise one or more computing devices in communication with the primary computer, such as tablets which herd managers utilize within the herd to facilitate the functions described or otherwise envisioned herein.

According to an embodiment, the herd management system functionality encompasses a software application that is installed on a herd management computing device and facilitates both communication with the primary or centralized herd management computing device, and the image-capturing and/or animal identification functionality described or otherwise envisioned herein. For example, a herd manager may download an app on their smartphone that facilitates image capture and animal identification. The app may prompt or otherwise enable image capture, may communication information to and from the central system, and may then provide animal identification to the herd manager via the user interface. According to another embodiment, the app communicates information to the central system but does not communicate the animal identification to the herd manager. According to yet another embodiment, the app provides instructions or other herd management information to the herd manager utilizing the app, thereby facilitating herd management. For example, after obtaining an image and identifying the animal using the vein recognition methods described or otherwise envisioned herein, the app may provide an identification and/or instructions to the herd manager, such as a name or other unique identifier for the animal, as well as milking, health, and/or other information about the identified animal.

Referring to FIG. 2, in one embodiment, is a flowchart of a method 200 for dairy animal identification and tracking, in accordance with an embodiment. At step 210 of the method, a system 100 is provided. System 100 can be any of the embodiments described herein or otherwise envisioned, and can include any of the components of the devices and components described in conjunction with FIG. 1, such as one or more devices 10 with imager 20, controller 22, and wireless communications module 30, and one or more processors 40 with database 42, among other elements. For example, system 100 may be a herd management system as described or otherwise envisioned herein.

According to just one embodiment, device 10 is a tablet, wearable, smartphone, or other portable or handheld computing device configured to capture an image of at least a portion of an udder 12. The device may be situated in a location where it will automatically capture images, such as a milking station, or may be a handheld device that requires positioning and/or activation by a user to take one or more images.

At step 220 of the method, the device 10 captures one or more images of at least a portion of an udder of a dairy animal. The image may be an RGB color photograph, a black and white photograph, thermal imaging, near-infrared spectroscopy, near-infrared imaging, and/or any of a variety of other formats. The image may be a composite or one or more formats. The image may be captured automatically or in response to a signal or trigger. For example, images may be captured continuously or periodically such as every second, 10 seconds, 30 seconds, minute, or any other timeframe, and analyzed for the existence of a vein pattern. According to another embodiment, images are captured when an animal is detected in the frame of view of the imager. The image may alternatively and/or additionally be captured only at the direction of the herd manager.

According to an embodiment, the system may identify which of a plurality of obtained images is best suited for vein analysis. This may comprise an analysis of one or more parameters of the images, a comparison of obtained images, a partial vein analysis of the images, and/or other method to identify one or several images from a plurality of images for subsequent analysis.

Figure 3:
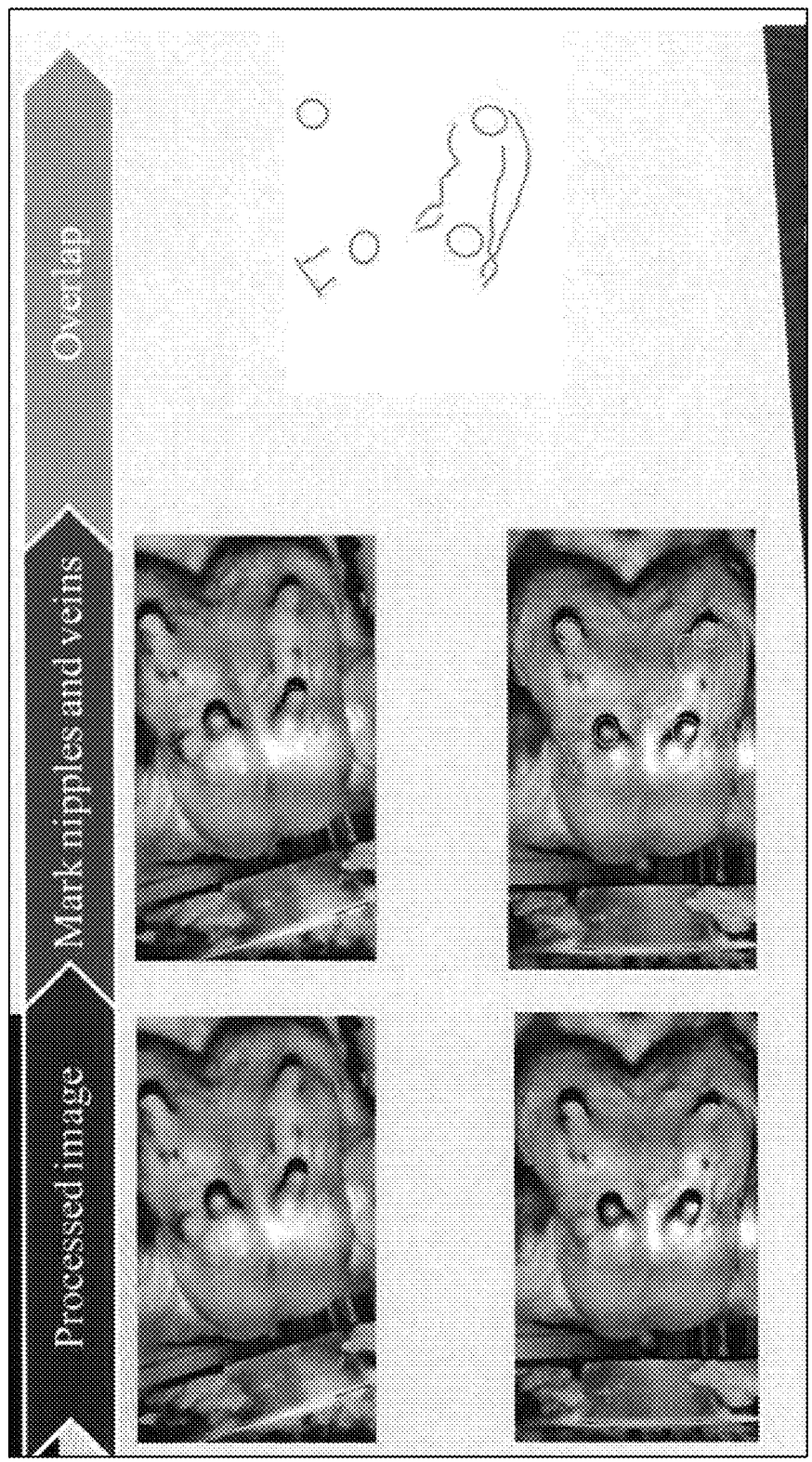
FIG. 3 is representation of vein pattern extraction, in accordance with an embodiment.
Figure 4:
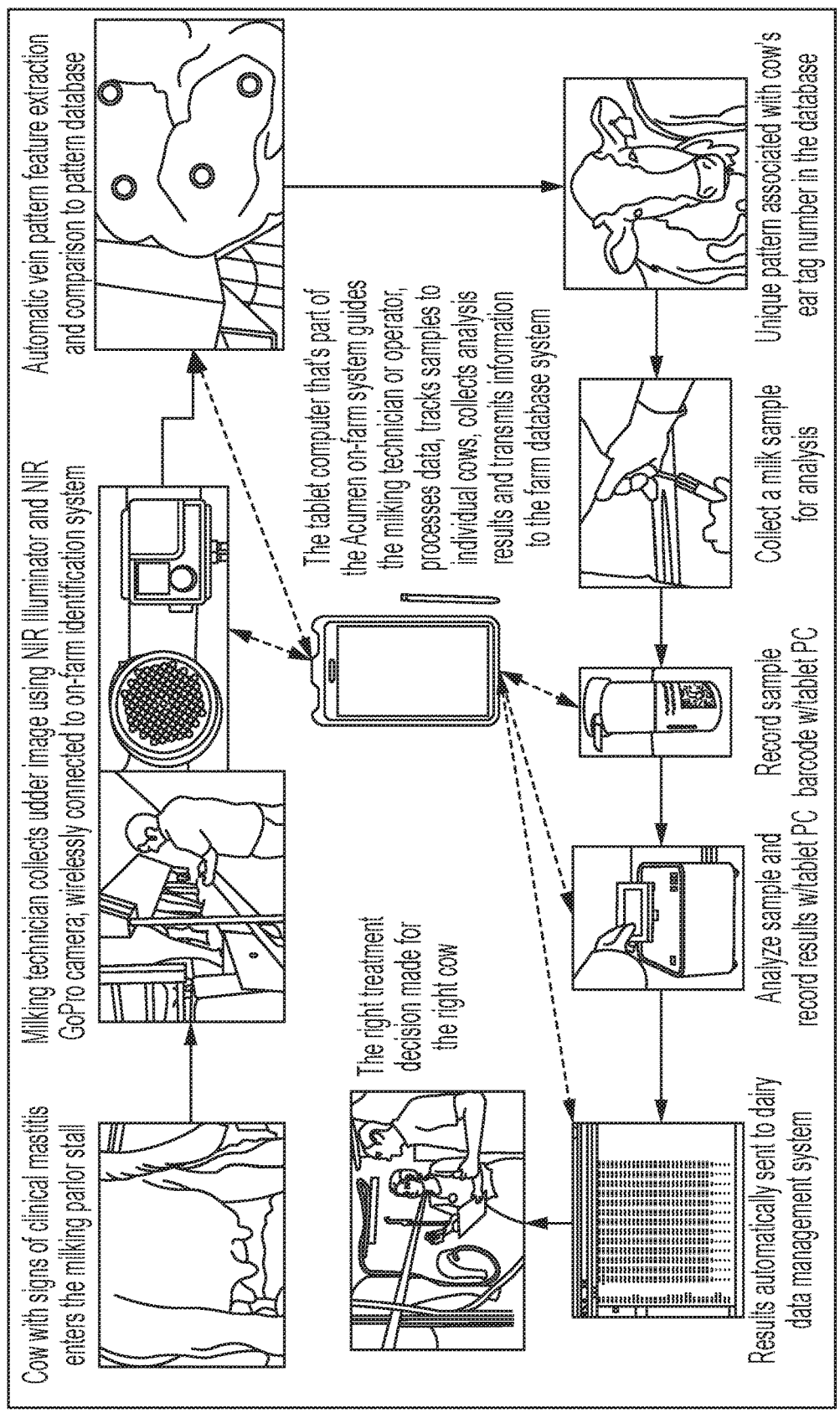
FIG. 4 is a representation of a dairy animal identification and tracking method, in accordance with an embodiment.

According to an embodiment, device 10 analyzes the images, and/or system 100 analyzes the image as described or otherwise envisioned herein. For example, device 10 may communicate the one or more obtained images to a central or primary herd management computer, server, or other computing device. This may be via any wired and/or wireless network. According to an embodiment, device 10 communicates only an identified or selected image for analysis, or device 10 communicates all obtained images to the primary herd management computing device for subsequent analysis. As just one example, device 10 is a table or smartphone utilized by a herd manager, and communicates one or more images via WiFi, Bluetooth, cellular, or other network to the backroom herd management computer, which may be a remotely-located computing device such as a SAAS solution. FIG. 3, in one embodiment, depicts a vein analysis/extraction methodology and outcome.

At step 230 of the method, the system analyzes the one or more images and extracts a vein pattern from the image. This could be performed, for example, by pattern recognition methodology, by comparing neighboring and/or non-neighboring pixels, by a process facilitated by machine learning, or via any of a variety of other methods. This methodology may also comprise, for example, identification of one or more of the teats of the animal in relation to the vein pattern.

According to an embodiment, the device 10 analyzes the one or more images and extracts a vein pattern from the image. According to another embodiment, the central herd management system computer performs the analysis to analyze the one or more images and extracts a vein pattern from the image.

At step 240 of the method, the system compares the extracted vein pattern to a database of stored vein patterns. For example, the images and/or the extracted vein pattern may be analyzed by device 10 and/or by the processor 40. Accordingly, the database of stored vein patterns may be one or both of databases/memory 26 and 42.

According to an embodiment, the device 10 compares the extracted vein pattern to a database of stored vein patterns. According to another embodiment, the central herd management system computer performs the analysis to compares the extracted vein pattern to a database of stored vein patterns.

According to an embodiment, the herd management system may determine that there is no match in the system for the extracted vein pattern. This may occur, for example, if the animal is being imaged for the first time. This may be upon installation of the system, or if a new animal is introduced to the herd. The system may then prompt the herd manager for additional information about the animal. In the case of a device 10 comprising a software app, for example, the app may prompt the user to enter, via a user interface, identifying information about the dairy animal. This could be performed via a free-text entry form, a series of predetermined prompts, or via other user interface mechanism. The user may also have the option to capture a new image if the animal should already be in the herd management system, but the image was not sufficient to identify the animal.

At step 250 of the method, the system identifies the imaged animal based on identification of a stored vein pattern that matches the extracted vein pattern. The match requirement may be above a certain threshold, for example, requiring a certain percentage of features to be similar between the extracted vein pattern and the stored vein pattern. According to an embodiment, the stored vein pattern is associated with an identifier unique to the animal, such as an ear tag, brand, or other identifier. System 100 may comprise a database of animals that comprises information about a unique identifier associated each animal, a vein pattern associated with each animal, a milking history associated with each animal, a health history associated with each animal, a genealogy associated with each animal, and/or any other information, parameter, or characteristic about the animal.

At optional step 260 of the method, the herd manager may associate information with the identified animal. For example, the device 10 or an associated device may comprise a user input that allows the herdsman to enter information or make a selection about the animal. It may be a text entry field, a button, a swipe, a touch, or any other method of data entry or selection. For example, the user interface may request an input whenever an animal is identified that is healthy or possibly not-healthy, or otherwise requires tracking. Suspicion of mastitis or another condition may also be associated with the animal, and/or may be provided by the herd manager. This may trigger handling of the milk in a manner different from other animals, such as diverting it to a different collection or location.

At optional step 270 of the method, a milk sample is collected from the animal for analysis, either immediately or at a later time. In the case of an animal suspected of suffering from mastitis, for example, the sample may be collected and sent to an on-site or off-site lab for analysis. Information about collection and analysis can be automatically associated with the animal in the herd management system, which can be performed via user interface of the computing device 10.

Similarly, at optional step 280 of the method, a herd management decision is made or selected for the animal. For example, the animal may be treated for a condition or disease, sent to a different location, or otherwise managed. The association between a sample or other data entry and the animal is facilitated by the imaging and identification system.

According to an embodiment, for example, device 10 comprises a software application that enables selection or entry of herd management decisions once an animal is identified. This could comprise health selections or entries, scheduling selections or entries, history selections or entries, milk collection selections or entries, and/or general information selections or entries, among many other possible selections and entries.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The above-described embodiments of the described subject matter can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single device or computer or distributed among multiple devices/computers.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. A method for identifying a dairy animal using a computing device comprising an imager, the method comprising the steps of:
   obtaining, via the imager of the computing device, at least one image of at least a portion of an udder of the dairy animal;
   extracting a vein pattern from the at least one image;
   comparing the extracted vein pattern to a database of stored extracted vein patterns, wherein each extracted vein pattern in the database is associated with an animal in a herd of dairy animals; and
   identifying, based on the comparison, the dairy animal in the database of stored extracted vein patterns.

2. The method of claim 1, further comprising the step of communicating the obtained at least one image to a central herd management computing device for the extracting, comparing, and/or identifying step(s).

3. The method of claim 1, wherein the computing device is a handheld computing device.

4. The method of claim 3, wherein the computing device is a tablet or smartphone.

5. The method of claim 1, further comprising the step of prompting a herd manager, if the extracted vein pattern does not match any of the stored extracted vein patterns, for information about the imaged dairy animal.

6. The method of claim 1, wherein the imager is a camera, a near-infrared spectroscope, or a thermal imager.

7. The method of claim 1, further comprising the step of selecting, based at least in part on the identification of the dairy animal, a management decision about the identified dairy animal.

8. The method of claim 1, further comprising the step of associating, based at least in part on the identification of the dairy animal, additional information about the identified animal in the database of stored extracted vein patterns.

9. A system for identifying a dairy animal, the system comprising:
   a database of stored extracted vein patterns, wherein each stored extracted vein pattern is associated with a specific dairy animal;
   a computing device comprising an imager configured to obtain at least one image of at least a portion of an udder of the dairy animal;
   a controller configured to: (i) extract a vein pattern from the at least one obtained image; (ii) compare the extracted vein pattern to one or more extracted vein patterns in the database of stored extracted vein patterns; and (iii) identify, based on said comparison, the dairy animal in the database of stored extracted vein patterns.

10. The system of claim 9, further comprising a communications module configured to communicate the obtained at least one image.

11. The system of claim 9, wherein said system is a herd management system, and wherein said computing device comprises a handheld computing device.

12. The system of claim 11, wherein the computing device is a tablet or smartphone.

13. The system of claim 9, wherein the controller is further configured to prompt a user, if the extracted vein pattern does not match any of the stored extracted vein patterns, for information about the imaged dairy animal.

14. The system of claim 9, wherein the imager is a camera, a near-infrared spectroscope, or a thermal imager.

15. The system of claim 9, wherein the controller is further configured to receive a selection from a user comprising a management decision about the identified dairy animal, wherein said management decision is based at least in part on the identification of the dairy animal.

16. The system of claim 9, wherein the controller is further configured to associate, based at least in part on the identification of the dairy animal, additional information about the identified animal in the database of stored extracted vein patterns.

17. A herd management computing device, the device comprising:
   an imager configured to obtain at least one image of at least a portion of an udder of the dairy animal;
   a controller configured to: (i) extract a vein pattern from the at least one obtained image; (ii) compare the extracted vein pattern to one or more extracted vein patterns in a database of stored extracted vein patterns, wherein each stored extracted vein pattern is associated with a specific dairy animal; and (iii) identify, based on said comparison, the dairy animal in the database of stored extracted vein patterns.

18. The herd management computing device of claim 17, wherein the device is a tablet or smartphone.

19. The herd management computing device of claim 17, wherein the controller is further configured to receive a selection from a user comprising a management decision about the identified dairy animal, wherein said management decision is based at least in part on the identification of the dairy animal.

20. The herd management computing device of claim 17, wherein the controller is further configured to associate, based at least in part on the identification of the dairy animal, additional information about the identified animal in the database of stored extracted vein patterns.

* * * * *